United States Patent

Wolleb

[11] Patent Number: 6,087,492
[45] Date of Patent: Jul. 11, 2000

[54] SUBSTITUTED PHTHALOCYANINES AND THEIR USE

[75] Inventor: Heinz Wolleb, Fehren, Switzerland

[73] Assignee: Ciba Specialty Chemicals Corporation, Tarrytown, N.Y.

[21] Appl. No.: 09/242,144

[22] PCT Filed: Sep. 24, 1997

[86] PCT No.: PCT/EP97/05223

§ 371 Date: Feb. 9, 1999

§ 102(e) Date: Feb. 9, 1999

[87] PCT Pub. No.: WO98/14520

PCT Pub. Date: Apr. 9, 1998

[30] Foreign Application Priority Data

Oct. 3, 1996 [CH] Switzerland .............................. 2404/96

[51] Int. Cl.⁷ .............................. G03C 1/92; G03C 5/06; G01D 9/00; C07D 487/22

[52] U.S. Cl. .......................... 540/139; 540/132; 540/129; 540/1.32; 540/136; 540/139; 540/140; 528/64.1; 430/270; 430/495

[58] Field of Search .................................... 540/136, 122, 540/132, 139, 129, 140; 430/270, 495; 428/64.1

[56] References Cited

U.S. PATENT DOCUMENTS

| | | | |
|---|---|---|---|
| 3,002,845 | 3/1961 | Haelzle | 106/288 |
| 3,006,921 | 10/1961 | Weinmayr | 260/314.5 |
| 3,646,006 | 2/1972 | Lord | 260/209 |
| 5,350,843 | 9/1994 | Itoh et al. | 540/138 |

(List continued on next page.)

FOREIGN PATENT DOCUMENTS

| | | |
|---|---|---|
| 0302497 | 2/1989 | European Pat. Off. . |
| 0373643 | 6/1990 | European Pat. Off. . |
| 0492508 | 7/1992 | European Pat. Off. . |
| 0511598 | 11/1992 | European Pat. Off. . |

(List continued on next page.)

OTHER PUBLICATIONS

Seiji et al., Chem Abst. 1989, 110: 97172. 1989.
Derwent Abstracts, 86–234553 (JP 61162396–Jul. 23, 1986).

(List continued on next page.)

*Primary Examiner*—Mukund J. Shah
*Assistant Examiner*—Pavanaram K Sripada
*Attorney, Agent, or Firm*—David R. Crichton

[57] ABSTRACT

This invention relates to a phthalocyanine or its metal complex of a divalent metal, oxometal, halogenometal or hydroxymetal, which comprises at least one unsubstituted or substituted formyl, carbonyl, hydroxymethyl or carboxyl group which as attached at the peripheral carbon skeleton. These phthalocyanines or their derivatives are used in recording layers of optical recording media.

There is also claimed a novel process for the preparation of some of these compounds corresponding to formula III

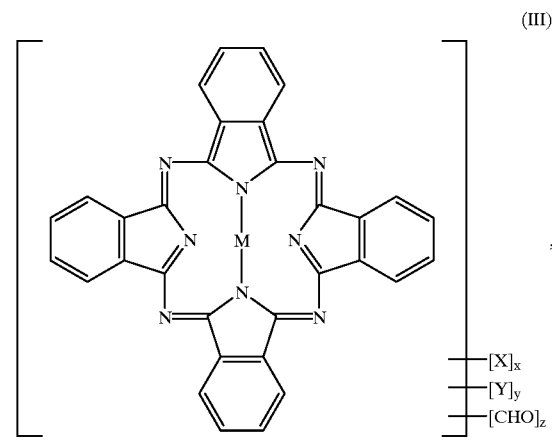

(III)

wherein

M is a divalent metal, oxometal, halogenometal or hydroxymetal, or 2 hydrogen atoms, X is halogen, or 2 X in vicinal position on a phenyl ring form together a —C=C—C=C— bridge so that an additional phenyl ring is obtained, Y is —OR$_1$, —OOC—R$_2$, —NHR$_1$, —N(R$_1$)R$_2$ or —SR$_1$, x is 0 or a number from 1 to 8, y depending on z is a number from z to 4, and z is a number from 1 to 4, by reacting a compound of formula IV

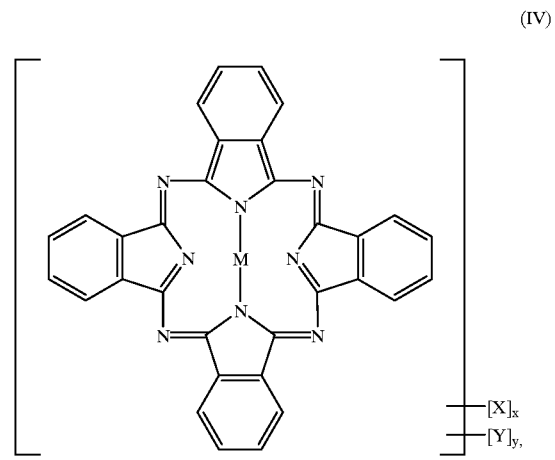

(IV)

wherein M, X, Y, x and y are as defined in formula III, with z mol each of dimethylformamide and phosphoryl chloride.

12 Claims, No Drawings

U.S. PATENT DOCUMENTS

| | | | |
|---|---|---|---|
| 5,409,634 | 4/1995 | Itoh et al. | 252/299.2 |
| 5,641,879 | 6/1997 | Wolleb et al. | 540/139 |
| 5,663,326 | 9/1997 | Wolleb | 540/139 |

FOREIGN PATENT DOCUMENTS

| | | |
|---|---|---|
| 850217 | 12/1939 | France . |
| 2020812 | 11/1971 | Germany . |
| 384114 | 1/1965 | Switzerland . |
| 801488 | 9/1958 | United Kingdom . |

OTHER PUBLICATIONS

Derwent Abstracts, 88–260319 (JP 63 188148–Aug. 3, 1988).

Derwent Abstracts N 71–727235 [46] (DE 2020812 A, filed Nov. 11, 1971).

Hall et al., Nouveau, Journal De Chimi, vol. 6, No. 12, pp. 653–658 (1982).

Kobayashi et al., J. American Chemical Society, vol. 112, pp. 9640–9641 (1990).

Kutney et al, Tetrahedron, vol. 27, pp. 3323–3330 1971.

Legnoff, et al., Tetrahedron Letters, vol. 30, No. 41, pp. 5555–5558 (1989).

Derwent Abstracts, 1990–145170 [19] (JP 02092963).

SUBSTITUTED PHTHALOCYANINES AND THEIR USE

This application is a 371 of PCT/EP97/05223 filed Sep. 24, 1997.

This invention relates to novel phthalocyanines or the derivatives thereof which are substituted by 1–4 formyl, carbonyl, hydroxymethyl or carboxyl groups, to their use in recording layers of optical recording media, as well as to a novel process for the preparation of some of these compounds.

The field of this invention is that of the optical recording of information on write-once recording media, the information bits differing in the different optical properties of a dye on written or unwritten places. This technology is usually called WORM (for example CD-R, SD-R, DVD-R or MMCD-R), which abbreviations have been adopted here.

The use of dyes which absorb radiation in the near infrared range (NIR range) for recording information in WORM systems (write once read many) has been known for some time and has been described, inter alia, by Emmelius in Angewandte Chemie, No. 11, pages 1475–1502 (1989). By irradiating such recording materials with laser it is possible to achieve the change in absorption required for recording information in binary form via physical changes (for example by sublimation or diffusion) or via chemical changes (for example photochromism, isomerisation or thermal degradation).

Substituted phthalocyanines are an important class of dyes for use in such WORM systems because they have high NIR absorptions in the range of 700 nm to 900 nm when, depending on the central metal atom, they are correspondingly peripherally substituted.

The most stringent requirements are placed on the recording layer to be used, such as high refractive index, high initial reflectivity, narrow absorption bands in the solid state, uniformity of the writing width at different pulse duration, high stability to light in daylight as well as under weak laser radiation (readout) coupled with high sensitivity to intense laser radiation (inscribing), low noise, high resolution as well as, most importantly, very little statistical jitter of the pits over a desired value at optimum writing performance.

As the recording layer is normally applied from a solution, typically by spin coating, the dyes must usefully be readily soluble in conventional solvents, which are described, inter alia, in EP 511 598.

Alkoxy-polysubstituted and halogenated phthalocyanines are known from EP 373 643 and EP 513 370. However, such compounds cannot be used singly but only as mixtures of many isomers. Analogous isomer mixtures having improved sufficient solubility are known from EP 703 280.

On the other hand, EP 712 904 discloses phthalocyanines substituted by phosphorus groups which have a low degradation temperature, a relatively narrow absorption band and a high refractive index at 780 nm and good contrast between written and unwritten places.

However, the known recording layers with readily soluble phthalocyanine dyes have the required properties only to an unsatisfactory extent, the optical resolution in particular often being not quite satisfactory. Moreover, the best products are noble metal phthalocyanines, the high material costs of which are irreconcilable with the demand for an inexpensive mass product which may be thrown into the rubbish.

Moreover, as the known soluble products are exclusively complicated isomer mixtures, it is imperative to use an extremely elaborate analytics for quality control.

Using specific phthalocyanine derivatives as recording layer, it has surprisingly been possible to provide an optical recording medium, the properties of which are astonishingly better than those of the recording media known to date. In addition, the phthalocyanine derivatives of this invention can be easily analysed and it is not necessary to choose a noble metal as central metal atom.

In one of its aspects, this invention relates to a phthalocyanine or its metal complex of a divalent metal, oxometal, halogenometal or hydroxymetal, which comprises at least one unsubstituted or substituted formyl, carbonyl, hydroxymethyl or carboxyl group attached at the peripheral carbon skeleton.

The divalent oxometal, halogenometal or hydroxymetal can additionally be coordinated to one, and the divalent metal can additionally be coordinated to one or two, neutral molecules which are independent or dependent on one another, which neutral molecules contain at least one hetero atom selected from the group consisting of N, O and S.

Divalent metals are, for example, Cu(II), Zn(II), Fe(II), Ni(II), Ru(II), Rh(II), Pd(II), Pt(II), Mn(II), Mg(II), Be(II), Ca(II), Ba(II), Cd(II), Hg(II), Sn(II), Co(II) or Pb(II). Divalent oxometals are, for example, V(IV)O, Mn(IV)O, Zr(IV)O or Ti(IV)O. Divalent halogenometals are, for example, Fe(III)Cl, In(III)Cl or Ce(III)Cl. Divalent hydroxymetals are, for example, Al(III)OH, Cr(III)OH, Bi(III)OH or Zr(IV)(OH)$_2$.

The groups attached at the peripheral carbon skeleton can be —CHO, —CO-KW$_{radical}$, —CH$_2$OH or —COOH, or unsubstituted or substituted formyl, hydroxymethyl or carboxyl groups which may be prepared from —CHO, —CO-KW$_{radical}$, —CH$_2$OH or —COOH by methods known per se. Substituted formyl or carbonyl groups are typically their acetals, oximes or hydrazones. Substituted hydroxymethyl groups are typically —CH$_2$—OOC-KW$_{radical}$ or —CH$_2$—O-KW$_{radical}$. Substituted carboxyl groups are typically esters or thioesters, such as —OO-KW$_{radical}$ or —COS-KW$_{radical}$, each KW$_{radical}$ being any saturated, unsaturated or aromatic unsubstituted or substituted hydrocarbon radical, for example C$_1$–C$_{20}$alkyl, C$_1$–C$_{20}$cycloalkyl, C$_1$–C$_{20}$alkenyl, C$_1$–C$_{20}$cycloalkenyl, C$_1$–C$_{20}$alkynyl, C$_1$–C$_{20}$cycloalkynyl, C$_6$–C$_{18}$aryl or C$_7$–C$_{18}$aralkyl.

A preferred compound is that of formula I

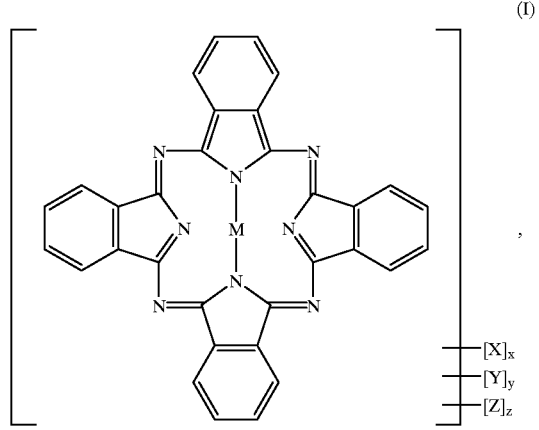

wherein

M is a divalent metal, oxometal, halogenometal or hydroxymetal, or 2 hydrogen atoms, X is halogen, or 2 X in vicinal position on a phenyl ring form together a —C=C—C=C— bridge so that an additional phenyl ring is obtained, Y is —R$_1$, —OOC—R$_2$, —NHR$_1$, —N(R$_1$)R$_2$ or —R$_1$, Z is —CHO, —CH(OR$_3$)OR$_4$, —CH═N—OH, —CH═N—OR$_3$, —CH═N—NHR$_5$, —CH═N—N(R$_3$)R$_5$, —CH$_2$OH, —CH$_2$OR$_3$, —CH$_2$OOC—R$_3$, —CO—R$_3$, —COOH or —COOR$_3$, x is 0 or a number from 1 to 8, y depending on z is a number from z to 4, and z is a number from 1 to 4, wherein R$_1$ to R$_5$ are each independently of one another C$_1$–C$_{20}$alkyl which is unsubstituted or substituted by halogen, hydroxy, C$_1$–C$_{20}$alkoxy, C$_1$–C$_{20}$alkylamino or C$_2$–C$_{20}$dialkylamino and which may be interrupted by —O—, —S—, —NH— or —NR$_6$—; C$_1$–C$_{20}$cycloalkyl, C$_1$–C$_{20}$alkenyl, C$_1$–C$_{20}$cycloalkenyl, C$_1$–C$_{20}$alkynyl, C$_1$–C$_{20}$cycloalkynyl, C$_6$–C$_{18}$aryl or C$_7$–C$_{18}$aralkyl, or R$_1$ and R$_2$ together are C$_2$–C$_{20}$alkylene which is unsubstituted or substituted by oxo, hydroxy or C$_1$–C$_{20}$carboxy and which may be interrupted by —O—, —S—, —NH— or —NR$_6$—, or R$_3$ and R$_4$ together are C$_2$–C$_{20}$alkylene which is unsubstituted or substituted by halogen, hydroxy, C$_1$–C$_{20}$alkoxy, C$_1$–C$_{20}$alkylamino or C$_2$–C$_{20}$dialkylamino, and R$_6$ is C$_1$–C$_{20}$alkyl, C$_1$–C$_{20}$cycloalkyl, C$_1$–C$_{20}$alkenyl, C$_1$–C$_{20}$cycloalkenyl, C$_1$–C$_{20}$alkynyl, C$_1$–C$_{20}$cycloalkynyl, C$_6$–C$_{18}$aryl or C$_7$–C$_{18}$aralkyl, and wherein the divalent oxometal, halogenometal or hydroxymetal may be additionally coordinated to one, and the divalent metal atom may additionally be coordinated to one or two, neutral molecules which are independent or dependent on one another, which neutral molecules contain at least one hetero atom selected from the group consisting of N, O and S.

Alkyl, alkenyl or alkynyl, e.g. C$_1$–C$_{20}$alkyl, C$_2$–C$_{20}$alkenyl or C$_2$–C$_{20}$alkynyl, can be straight-chain, branched, monocyclic or polycyclic. Accordingly, C$_1$–C$_6$alkyl is typically methyl, ethyl, n-propyl, isopropyl, n-butyl, sec-butyl, isobutyl, tert-butyl, cyclobutyl, n-pentyl, 2-pentyl, 3-pentyl, 2,2-dimethylpropyl, cyclopentyl, n-hexyl, cyclohexyl and, in addition, C$_1$–C$_{20}$alkyl is typically n-octyl, 1,1,3,3-tetramethylbutyl, 2-ethylhexyl, nonyl, trimethylcyclohexyl, decyl, menthyl, thujyl, bornyl, 1-adamantyl, 2-adamantyl, dodecyl, tetradecyl, hexadecyl, octadecyl or eicosyl.

C$_2$–C$_{20}$Alkenyl is mono- or polyunsaturated C$_2$–C$_{20}$alkyl, wherein two or more double bonds may be isolated or conjugated, typically vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-bututen-3-yl, 2-methyl-3-buten-2-yl, 3-methyl-2-buten-1-yl, 1,4-pentadien-3-yl, 2-cyclopenten-1-yl, 2-cyclo hexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the different isomers of hexenyl, octenyl, nonenyl, decenyl, dodecenyl, tetradecenyl, hexadecenyl, octadecenyl, eicosenyl, heneicosenyl, docosenyl, tetracosenyl, hexadienyl, octadienyl, nonadienyl, decadienyl, dodecadienyl, tetradecadienyl, hexadecadienyl, octadecadienyl or eicosadienyl.

C$_2$–C$_{20}$Alkynyl is C$_2$–C$_{20}$alkyl or C$_2$–C$_{20}$alkenyl which is doubly mono- or polyunsaturated and wherein the triple bonds may be isolated or may be conjugated with each other or with double bonds, typically 1-propyn-3-yl, 1-butyn4-yl, 1-pentyn-5-yl, 2-methyl-3-butyn-2-yl, 1,4-pentadiin-3-yl, 1,3-pentadiin-5-yl, 1-hexyn-6-yl, cis-3-methyl-2-penten-4-yn-1-yl, trans-3-methyl-2-penten-4-yn-1-yl, 1,3-hexadiin-5-yl, 1-octyn-8-yl, 1-nonyn-9-yl, 1-decyn-10-yl or 1-eicosin-20-yl.

C$_7$–C$_{18}$Aralkyl is typically benzyl, 2-benzyl-2-propyl, β-phenylethyl, 9-fluorenyl, α,α-dimethylbenzyl, ω-phenylbutyl, ω-phenyloctyl, ω-phenyldodecyl or 3-methyl-5-(1',1',3',3'-tetramethyl)-butylbenzyl. In addition, C$_7$–C$_{24}$aralkyl can typically also be 2,4,6-tri-tert-butylbenzyl or 1-(3,5-dibenzylphenyl)-3-methyl-2-propyl. If C$_7$–C$_{18}$aralkyl is substituted, then the alkyl as well as the aryl moiety of the aralkyl group may be substituted, the latter alternative being preferred.

C$_6$–C$_{18}$Aryl is typically phenyl, naphthyl, biphenylyl, 2-fluorenyl, phenanthryl, anthracenyl or terphenylyl.

C$_1$–C$_{20}$Alkylamino is —NH—C—C$_{20}$alkyl, typically methylamino, ethylamino, propylamino, hexylamino or octylamino. C$_2$–C$_{20}$Dialkylamino is

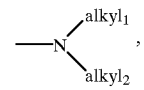

wherein the number of carbon atoms in both alkyl groups totals 2 to 20, e.g. dimethylamino, diethylamino, dipropylamino, dibutylamino, methyihexylamino, ethylhexylamino, octyldodecylamino or ethyloctadecylamino.

Halogen is chloro, bromo, fluoro or iodo.

Coordinated neutral molecules may be customary ligands suitable for transition metals, for example water, amines, ammonia, hydrazine, triethylamine, carbon monoxide, nitrogen monoxide, acetone or heteroaromatic compounds, such as pyridine, quinoline, furan, pyrrole, thiophene or methylimidazole.

M is preferably H$_2$, Cu(II), Zn(II), Ni(II), Pd(II), Pt(II), Mn(II) or Co(II), particularly preferably H$_2$, Cu(II), Zn(II) or Pd(II), very particularly preferably Cu(II).

X is preferably chloro or bromo, particularly preferably bromo.

Y is preferably —OR$_1$ or —OOC—R$_2$, particularly preferably —OR$_1$.

Z is preferably —CHO, —CH(OR$_3$)OR$_4$, —CH$_2$OH, —CH$_2$OOC—R$_3$, —CO—R$_3$, —COOH or —COOR$_3$, particularly preferably —CHO, —CH(OR$_3$)OR$_4$, —CH$_2$OH, —CH$_2$OOC—R$_3$ or —CO—R$_3$.

x is preferably 0 or a number from 1 to 8, particularly preferably 0 or a number from 2 to 4.

y is preferably 2, 3 or 4, particularly preferably 4.

z is preferably 1 or 2, particularly preferably 1.

R$_1$ is preferably unsubstituted C$_4$–C$_8$alkyl which may be interrupted by —O—, particularly preferably secondary unsubstituted C$_4$–C$_8$alkyl which is branched several times.

R$_2$ is preferably unsubstituted C$_1$–C$_8$alkyl which may be interrupted by —O—, particularly preferably unsubstituted C$_1$–C$_3$alkyl.

If R$_1$ and R$_2$ together form a group, then this group is preferably C$_4$–C$_8$alkylene which is unsubstituted or substituted by oxo, hydroxy or C$_1$–C$_{20}$carboxy and which may be interrupted by —O—, —NH— or —NR$_6$—, particularly preferably —(CH$_2$)$_4$—, —(CH$_2$)$_5$—, —(CH$_2$)$_2$O(CH$_2$)$_2$—, —(CH$_2$)$_2$N(CH$_3$)(CH$_2$)$_2$—, —(CH$_2$)$_2$NH(CH$_2$)$_2$—, —C(CH$_3$)

$_2CH_2COCH_2C(CH_3)_2-$, $-C(CH_3)_2CH_2CH(OH)CH_2C(CH_3)_2-$ or $-C(CH_3)_2CH_2CH(OCOCH_3)CH_2C(CH_3)_2-$ and, very particularly preferably, $-(CH_2)_4-$, $-(CH_2)_5-$ or $-(CH_2)_2O(CH_2)_2-$.

$R_3$ is preferably unsubstituted $C_1$–$C_4$alkyl which may be interrupted by —O—, particularly preferably methyl, ethyl or 3-oxa-1-pentyl.

$R_4$ is preferably unsubstituted $C_1$–$C_4$alkyl which may be interrupted by —O—, particularly preferably methyl, ethyl or 3-oxa-1-pentyl.

If $R_3$ and $R_4$ together form a group, then this group is preferably unsubstituted or hydroxy- or $C_1$–$C_8$alkoxy-substituted $C_2$–$C_{20}$alkylene, particularly preferably $-(CH_2)_2-$, $-(CH_2)_3-$ or $-CH_2-CH(CH_2OH)-$.

$R_5$ is preferably tertiary $C_4$–$C_{12}$alkyl or phenyl which is unsubstituted or substituted by halogen, hydroxy, $C_1$–$C_{20}$alkoxy, $C_1$–$C_{20}$alkylamino or $C_2$–$C_{20}$dialkylamino.

$R_6$ is preferably $C_1$–$C_4$alkyl, particularly preferably methyl or ethyl.

A particularly preferred compound is that of formula IIa, IIb, IIc or IId, (IIa)

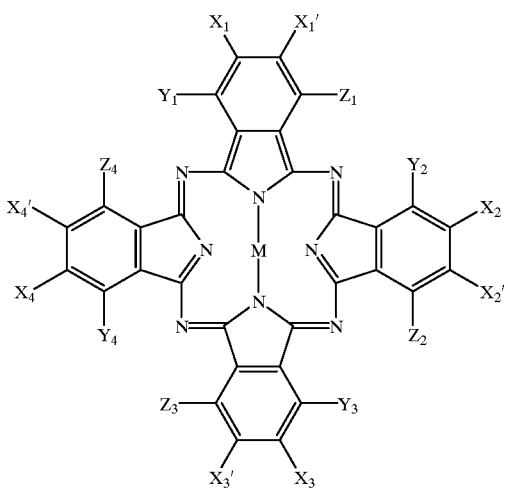

(IIb)

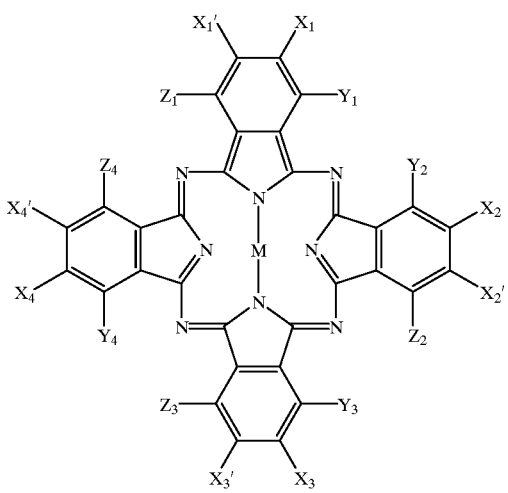

(IIc)

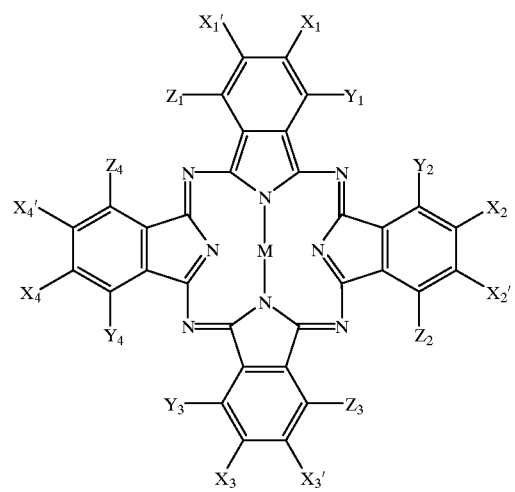

(IId)

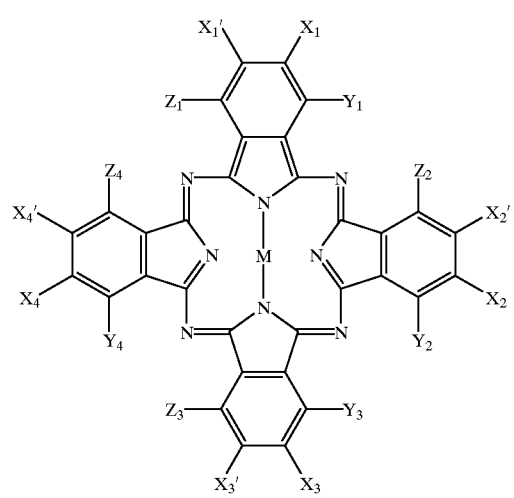

or a mixture of two or more compounds selected from the compounds of formulae IIa, IIb, IIc and IId, wherein M is a divalent metal, oxometal, halogenometal or hydroxymetal, or 2 hydrogen atoms, $X_1$ to $X_4$ and $X_1'$ to $X_4'$ are each independently of one another hydrogen or halogen, $Y_1$ to $Y_4$ are each independently of one another hydrogen or —$OR_1$, $Z_1$ is —CHO, —CH(OR$_3$)OR$_4$, —CH=N—OH, —CH=N—OR$_3$, —CH=N—NHR$_5$, —CH=N—N(R$_3$)R$_5$, —CH$_2$OH, —CH$_2$OR$_3$, —CH$_2$OOC—R$_3$, —CO—R$_3$, —COOH or —COOR$_3$, and $Z_2$ to $Z_4$ are each independently of one another hydrogen or a group $Z_1$, with the proviso that the number of those substituents $Y_1$ to $Y_4$ which are not hydrogen is at least equal to the number of those substituents $Z_1$ to $Z_4$ which are not hydrogen, and where $R_1$ to $R_5$ are as defined for formula I, and the divalent oxometal, halogenometal or hydroxymetal may additionally be coordinated to one, and the divalent metal atom may additionally be coordinated to one or two, neutral molecules which are independent or dependent on one another, which neutral molecules contain at least one hetero atom selected from the group consisting of N, O and S.

Particularly preferred is a mixture of 2 to 8 isomeric compounds corresponding to the compounds of formulae IIa, IIb, IIc and/or IId.

The novel phthalocyanines carrying —CHO, —CH$_2$OH or —COOH groups can be prepared in general analogy to methods known per se which are described, inter alia, in Nouveau Journal de Chimie, 6, 653–8 (1982), Tetrahedron Letters 30/41, 5555–8 (1989), J. Am. Chem. Soc. 112, 9640–1 (1990), EP 373 643 and EP 492 508. These reactions are carried out, for example, starting from one or several substituted phthalodinitriles or diiminoisoindolines, of which at least one is substituted by —CHO, —CH$_2$OH, —COOH or by a derivative thereof. Depending on the educts and the reaction conditions, pure compounds, or also product mixtures, are obtained from which the desired compounds can be isolated by conventional separation methods, such as chromatography. Before or after their condensation to the phthalocyanine, the —CHO, —CH$_2$OH and —COOH groups can be converted into one another by known methods reductively or oxidatively, or can be substituted. Disadvantages of these methods are, however, their generally unsatisfactory yield and the great difficulty of obtaining well defined products having only few components.

The novel phthalocyanines carrying —CHO, —CH$_2$OH or —COOH groups are therefore preferably prepared by the novel method of synthesis described hereinafter which, very surprisingly, gives the phthalocyanines preferred according to this invention in remarkably good yield with good selectivity. Considering the small number of components, these products have a surprisingly good solubility in the conventional spin coating solvents.

In principle, one or several formyl groups are introduced into a substituted phthalocyanine, which formyl groups can subsequently be converted by known methods oxidatively or reductively into hydroxymethyl or carboxyl groups as well as into other derivatives.

The formylation of phthalocyanines is novel. The reason for this is probably that the formylation of the most conventional known phthalocyanines, such as unsubstituted or chlorinated copper phthalocyanine, normally fails completely or gives only traces of formylated products which cannot be isolated.

Formyl groups can in principle be introduced by a great number of different methods of synthesis which may be found, inter alia, in the well known compendium "Compedium of Organic Synthetic Methods" (I. T. Harrison+Sh. Harrison, John Wiley & Sons). One of these methods is the formylation of aromatic compounds using dimethylformamide and phosphoryl chloride, which is also known as Vilsmeier reaction. According to Tetrahedron 27, 3323–30 (1971), in the case of 3-methylfuran this reaction gives a mixture of two isomers at a ratio of 14:1.

Very surprisingly, it has been found that the Vilsmeyer reaction proceeds with good selectivity in certain substituted phthalocyanines and affords excellent yields. The products can easily be isolated in sufficiently pure form for use in optical recording media.

Accordingly, this invention also relates to a process for the preparation of a compound of formula III (III)

[structure with substituents [X]$_x$, [Y]$_y$, [CHO]$_z$]

wherein M, X, Y, x, y and z are as defined for formula I, by reacting 1 mol of a compound of formula IV (IV)

[structure with substituents [X]$_x$, [Y]$_y$]

wherein M, X, Y, x and y are as defined for formula III, with z mol each of dimethylformamide and phosphoryl chloride.

The compounds of formula III at the same time preferably also correspond to formula IIa, IIb, IIc or IId, the identity, number and positions of groups X and Y remaining unchanged in the reaction of IV to III.

The educts of formula IV used in this process are known substances which can be prepared, for example, by methods according to, or analogous to, those described in Nouveau Journal de Chimie, 6, 653–8 (1982), Tetrahedron Letters 30/41, 5555–8 (1989), J. Am. Chem. Soc. 112, 9640–1 (1990), EP 373 643, EP 492 508 or EP 703 281.

This reaction can be carried out under the conditions known to the skilled person for the Vilsmeier reaction for aromatic compounds and which are disclosed, inter alia, in Houben-Weyl, Vols. 7/1, 16–44 (1954) and E3, 3–115 (1983) [Georg Thieme Verlag]. It is preferably carried out in an inert solvent and under inert gas, typically in an aromatic solvent, preferably under nitrogen in chlorobenzene. It is preferred first to react equimolar amounts of dimethylformamide and phosphoryl chloride under inert gas, and then to add the phthalocyanine to be formylated dissolved in an inert solvent, the temperature subsequently being raised. In the first reaction step, the temperature is preferably in the range from −100 to 50° C., particularly preferably from −30 to 25° C., and in the last reaction step it is preferably raised to 0 to 150° C., particularly preferably to 50 to 100° C.

The acylated phthalocyanines are also prepared by methods known per se. It is preferred to use the Friedel-Crafts acylation which is a commonly known method. The acylation can be carried out under Friedel-Crafts conditions analogous to the acylation of naphthalocyanines described in JP 02/92963. Surprisingly, it has been found that the Friedel-Crafts acylation of the novel phthalocyanines proceeds advantageously selectively.

The novel phthalocyanines can be used with excellent results as dyes for optical recording media.

Accordingly, this invention also relates to an optical recording medium, comprising a substrate, a recording layer and a reflecting or partially reflecting layer, the recording layer containing a novel phthalocyanine. The inventive optical recording medium can of course also contain more than one recording layer and/or more than one reflecting or partially reflecting (semi-transparent) layer.

The substrate functioning as a support for the layers applied to it is conveniently semi-transparent (T≧10%) or, preferably, transparent (T≧90%). The support can have a thickness of 0.01 to 10 mm, preferably of 0.1 to 5 mm.

The recording layer is preferably arranged between the transparent substrate and the reflecting layer. The thickness of the recording layer is from 10 to 1000 nm, preferably from 50 to 500 nm, particularly preferably about 100 nm, for example from 80 to 150 nm. The absorption of the recording layer is typically from 0.1 to 1.5 at the absorption maximum. With very particular preference, the layer thickness is chosen in a known manner, dependent on the respective refractive indices in the written and the unwritten state at the readout wavelength, such that there is constructive interference in the unwritten state and destructive interference in the written state, or vice versa.

The reflecting layer, which can be from 10 to 150 nm thick, preferably has a high reflectivity (R≧70%) coupled with a low transparency (T≦10%).

The layer which is topmost depending on the layer structure, for example the reflection layer or the recording layer, is conveniently additionally provided with a protective layer, which can have a thickness from 0.1 to 1000 μm, preferably from 0.1 to 50 μm and, particularly preferably, from 0.5 to 15 μm. This protective layer may, if desired, also serve as an adhesion promoter for a second substrate layer applied thereon, which is preferably from 0.1 to 5 mm thick and consists of the same material as the support substrate.

The reflectivity of the entire recording medium is preferably at least 45%, particularly preferably at least 60%.

The use of dyes of this invention results in advantageously homogeneous, amorphous and low-scatter recording layers, the absorption edge of which is steep in the solid phase. Further advantages are the high stability to light under daylight and under low-density laser radiation and at the same time the high sensitivity under high-density laser radiation, the uniform writing width, the good thermostability and storage stability as well as, in particular, the high optical resolution and the very small jitter.

Examples of suitable substrates are glasses, minerals, ceramics and thermosets or thermoplastics. Preferred supports are glasses and homo- or copolymeric plastics. Examples of suitable plastics are thermoplastic polycarbonates, polyamides, polyesters, polyacrylates and polymethacrylates, polyurethanes, polyolefins, polyvinyl chloride, polyvinylidene fluoride, polyimides, thermosetting polyesters and epoxy resins. The substrate can be in pure form or can also contain customary additives, for example UV absorbers or dyes, as is proposed, inter alia, in JP 04/167 239 as light protection for the recording layer. In the latter case it may be convenient for the dye added to the support substrate to have an absorption maximum which is hypsochromically shifted by at least 10 nm, preferably by at least 20 nm, relative to the dye of the recording layer.

The substrate is advantageously transparent in at least part of the range from 600 to 830 nm, so that it is permeable to at least 90% of the incident light of the writing or readout wavelength. On the side of the coating the substrate preferably has a spiral guide groove with a groove depth from 50 to 500 nm, a groove width from 0.2 to 0.8 μm and a radial distance between 2 adjacent turns from 0.4 to 1.6 μm, particularly preferably having a groove depth of 100 to 300 nm and a groove width of 0.3 μm to 0.6 μm.

Instead of the substrate, the recording layer itself can have a guide groove, as is described, inter alia, in EP 392 531.

The recording layer can consist exclusively or essentially of one or more novel phthalocyanines. To increase the stability still further, however, it is also possible if desired to add known stabilisers in customary amounts, for example a nickel dithiolate described in JP 04/025 493 as light stabiliser. If desired, it is also possible to add additional dyes, although the amount of such dyes is conveniently not more than 50% by weight, preferably not more than 10% by weight, based on the recording layer. Since the advantages of the novel recording media are based on the novel phthalocyanines, it is advantageous for the optionally added dye to have a hypsochromically shifted absorption maximum relative to the novel phthalocyanine, and for the amount of the added dye to be kept so small that the proportion of the latter in the overall absorption of the recording layer in the region from 600 to 830 nm is not more than 20%, preferably not more than 10%. With particular preference, however, no additional dye is added.

A particularly suitable reflective material for the reflection layer comprises metals which are good reflectors of the laser radiation used for recording and reproduction, examples being the metals of the third, fourth and fifth main groups and subgroups of the Periodic Table of the chemical elements. Particularly suitable metals are Al, In, Sn, Pb, Sb, Bi, Cu, Ag, Au, Zn, Cd, Hg, Sc, Y, La, Ti, Zr, Hf, V, Nb, Ta, Cr, Mo, W, Fe, Co, Ni, Ru, Rh, Pd, Os, Ir, Pt and the lanthanide metals Ce, Pr, Nd, Pm, Sm, Eu, Gd, Tb, Dy, Ho, Er, Tm, Yb and Lu, and also alloys thereof. For reasons of high reflectivity and ease of preparation, particular preference is given to a reflection layer of aluminium, silver, copper, gold or their alloys.

Suitable materials for the protective layer are predominantly plastics, which are applied in a thin layer either directly or with the aid of adhesion layers to the support or the topmost layer. It is judicious to choose mechanically and thermally stable plastics having good surface properties, which can be additionally modified, for example written on. The plastics can either be thermosets or thermoplastics. Preference is given to radiation-cured (for example using UV radiation) protective layers, which are particularly easy and economic to prepare. Large numbers of radiation-curable materials are known. Examples of radiation-curable monomers and oligomers are acrylates and methacrylates or diols, triols and tetrols, polyimides of aromatic tetracarboxylic acids and aromatic diamines having $C_1$–$C_4$ alkyl groups in at least two positions ortho to the amino groups, and oligomers containing dialkyl groups, for example dimethylmaleimidyl groups.

The novel recording media can also feature additional layers, for example interference layers. It is also possible to construct recording media having a plurality of (for example two) recording layers. The construction and use of such materials are known to the skilled person. If such layers are present, preference is given to interference layers which are disposed between the recording layer and the reflecting layer and/or between the recording layer and the substrate and which consist of a dielectric material, for example as described in EP 353 393 consisting of $TiO_2$, $Si_3N_4$, ZnS or silicone resins.

The novel recording media can be prepared by processes known per se, it being possible to employ various coating methods depending on the materials used and on their functioning.

Examples of suitable coating methods are dipping, flow coating, spreading, knife coating and spin coating, and also high-vacuum vapour deposition methods. When using flow coating methods, for example, solutions in organic solvents are generally used. When using solvents, care should be taken to ensure that the supports used are insensitive to these solvents. It is a particular advantage of the novel dyes that, even as pure compounds or as mixture of only few compnents, they are well soluble in less polar solvents, making it possible to forego the use of agressive solvents such as acetone. Examples of suitable coating methods and solvents are described in EP 401 791.

The recording layer is preferably applied by spin coating a dye solution, solvents that have been found appropriate being, in particular, alcohols such as 2-methoxy-ethanol, isopropanol, isobutanol or n-butanol or, preferably, fluorinated alcohols such as 2,2,2-trifluoroethanol or 2,2,3,3-tetrafluoro-1-propanol, and mixtures thereof.

The metallic reflection layer is preferably applied by sputtering or vapour deposition under vacuum. The sputtering technique is particularly preferred on account of the high degree of adhesion to the support for the application of the metallic reflection layer. This technique is described in detail in textbooks (e.g. J. L. Vossen and W. Kern, "Thin Film Processes", Academic Press, 1978) as well as in the state of the art (e.g. EP 712 904).

The structure of the novel recording medium depends principally on the readout method; known functional principles are the measurement of the change in transmission or, preferably, in reflection.

If the recording material is constructed in accordance with the change in reflection, then the following structures are examples of those which can be employed: transparent support/recording layer (one or more layers)/reflection layer and, if useful, protective layer (not necessarily transparent), or support (not necessarily transparent)/reflection layer/recording layer and, if useful, transparent protective layer. In the former case the light is irradiated from the support side, while in the latter case the radiation is incident from the side of the recording layer or, if appropriate, from the side of the protective layer. In both cases the light detector is on the same side as the light source. The former construction of the recording material to be used in accordance with the invention is generally preferred.

If the recording material is constructed in accordance with change in light transmission, the following alternative structure is a suitable example: transparent support/recording layer (one or more layers) and, if useful, transparent protective layer. The light for recording and for readout can be irradiated alternatively from the support side or from the side of the recording layer or, if appropriate, from the side of the protective layer, the light detector in this case always being on the opposite side.

Recording (inscribing, writing) and reading out the information is preferably carried out using laser radiation. Examples of suitable lasers are commercial semiconductor diode lasers, typically GaAsAl, InGaAIP, GaAs or GaN laser diodes with a wavelength of 635, 650, 670, 680, 780 or 830 nm, or 390–430 nm, or gas/ion lasers, typically He/Ne, Kr, HeCd or Ar laser with a wavelength of 602, 612, 633, 647, or 442 and 457 nm.

Recording is preferably effected by inscribing pits of variable length using laser radiation which is pulse duration-modulated and focussed on the recording layer. Depending on the focus geometry and the laser performace, the recording layer is, for example, 0.01–100 m/s and, preferably, 1–10 m/s.

The readout of the information is preferably carried out by spatially resolved measurement of the reflection or transmission using laser radiation of low capacity and a photodetector, it being particularly advantageous that laser radiation of the wavelength used for recording may be employed, so that no second laser apparatus need be used. Accordingly, in a preferred embodiment of the invention the information is recorded and readout at the same wavelength. During readout, the capacity of the laser is usually reduced over the laser radiation used for recording, e.g. from ten to fifty times. In the recording material used according to this invention, the information can be readout once or several times. Suitable photodetectors preferably include PIN and AV photodiodes as well as CCD (charge-coupled devices).

The novel process makes it possible to record information with a high degree of reliability and durability and these recordings are distinguished by having excellent mechanical and thermal stability, high stability to light and sharp edge zones of the optical pits. Particular advantages are the high signal/noise ratio as well as the high optical resolution which permits flawless recording and readout of the signals even, surprisingly, at high speed ($\geq 4\times$) (little jitter).

The novel medium is, in particular, an optical information medium of the WORM type. It can be used, for example, as a playable CD (compact disc), as storage material for computers or as an identity and security card, or for the production of diffractive optical elements such as holograms.

The invention therefore also relates to the use of the novel recording medium for optical recording, storage and reproduction of information, for the production of diffractive optical elements or for the recording of holograms. Recording and reproduction preferably take place in the wavelength range from 400 to 500 nm or, particularly preferably, from 600 to 830 nm.

The following Examples illustrate the invention in more detail:

EXAMPLE A1

A 100 ml three-necked flask, equipped with thermometer, dropping funnel, reflux condenser and nitrogen inlet, is charged with 2.19 g (30 mmol) of dimethylformamide (DMF) dried over molecular sieve 4A and cooled, with stirring, to 3° C. under an inert gas atmosphere. Over 10 min, 4.60 g (30 mmol) of freshly distilled phosphoryl chloride ($POCl_3$) are added dropwise and the clear colourless liquid is then stirred for 30 min at 23° C. Subsequently, 5.38 g (5 mmol) of tetra($\alpha$-2,4-dimethyl-3-pentyloxy)palladium phthalocyanine (prepared according to EP 712 904) in 50 ml of chlorobenzene (dried over molecular sieve 4A) are added and the mixture is heated for 6 hours to 95° C. After cooling to 23° C., 5.5 g of sodium acetate in 20 ml of water are added and the mixture is stirred for 15 min. This mixture is extracted with 200 ml of ethyl acetate and the organic phase is washed with 50 ml of 10% $NaHCO_3$ solution and 3×50 ml of saturated NaCl solution and then dried over MgSO$_4$, filtered and concentrated by evaporation. The green residue is purified by flash chromatography (Ø9 cm, hexanelethyl acetate=9:1), giving 4.62 g (83.7% of theory) of a green solid monoformyl-tetra(α-2,4-dimethyl-3-pentyloxy) palladium phthalocyanine having a $\lambda_{max}$ of 703 nm in N-methylpyrrolidone (NMP).

IR spectrum (KBr): 2960–2880 (s), 1680 (s), 1590 (s), 1490 (s). MALDI MS: (M+H)$^+$=1104.7 Da.

The NMR (500 MHz, CDCl$_3$) shows the product to be selectively monoformylated, one single aldehyde group being in para-position to one of the alkoxy radicals.

EXAMPLE A2

A 50 ml three-necked flask, equipped with magnetic stirrer, thermometer, dropping funnel, reflux condenser and nitrogen inlet, is charged with 1.14 9 (15.56 mmol) of DMF (dried over molecular sieve 4A) and then cooled, with stirring, to 3° C. under an inert gas atmosphere. Over 10 min, 2.39 g (15.56 mmol) of POCl$_3$ (freshly distilled) are added dropwise and the clear colourless liquied is then stirred for 30 min at 23° C. Subsequently, 2 g (1.95 mmol) of tetra(α-2,4-dimethyl-3-pentyloxy)copper phthalocyanine (prepared according to EP 712 904) in 20 ml of chlorobenzene (dried over molecular sieve 4A) are added and the mixture is heated for 6.5 hours to 95° C. After cooling to 23° C., 2 g of sodium acetate in 8 ml of water are added and the mixture is then stirred for 30 min. This mixture is extracted with 100 ml of ethyl acetate and the organic phase is washed with 50 ml of 10% NaHCO$_3$ solution and 2×50 ml of saturated NaCl solution and then dried over MgSO$_4$, filtered and concentrated by evaporation. The green residue is purified by flash chromatography (Ø4 cm, hexane/ethyl acetate=11:1), giving 0.79 9 (38.5% of theory) of green solid monoformyl-tetra (α-2,4-dimethyl-3-pentyloxy)copper phthalocyanine having a $\lambda_{max}$ (NMP) of 714 nm.

IR spectrum (KBr): 3700–3300 (m), 2960–2880 (s), 1680 (s), 1590 (s), 1490 (s).

EXAMPLE A3

A 50 ml three-necked flask, equipped with magnetic stirrer, thermometer, dropping funnel, reflux condenser and nitrogen inlet, is charged with 1.20 g (16.47 mmol) of DMF (dried over molecular sieve 4A) and cooled, with stirring, to 3° C. under an inert gas atmosphere. Over 10 min, 2.53 g (16.47 mmol) of POCl$_3$ (freshly distilled) are added dropwise and the clear colourless liquid is then stirred for 30 min at 23° C. Subsequently, 2 g (2.06 mmol) of tetra(α-2,4-dimethyl-3-pentyloxy)phthalocyanine (prepared according to M. J. Cook, J. Chem. Soc. Perkin Trans. I, 2453 (1988)) in 20 ml chlorobenzene (dried over molecular sieve 4A) are added and the mixture is heated for 5.5 hours to 95° C. After cooling to 23° C., 2 g of sodium acetate in 8 ml of water are added and the mixture is stirred for 30 min. This mixture is extracted with 100 ml of ethyl acetate and the organic phase is washed with 50 ml of 10% NaHCO$_3$ solution and 2×50 ml of saturated NaCl solution and then dried over MgSO$_4$, filtered and concentrated by evaporation. The green residue is purified by flash chromatography (Å4 cm, hexane/ethyl acetate=12:1), giving 1.21 g (58.9% of theory) of green solid metal-free monoformyl-tetra(α-2,4-dimethyl-3-pentyloxy) phthalocyanine having a $\lambda_{max}$ (NMP) of 728 nm.

IR spectrum (KBr): 3700–3300 (m), 2960–2880 (s), 1680 (s), 1590 (s), 1490 (s).

EXAMPLE A4

A 250 ml three-necked flask, equipped with magnetic stirrer, thermometer and nitrogen inlet, is charged with 1.58 g (1.43 mmol) of the monoformylated product of Example A1 in 100 ml of ethanol/tetrahydrofuran (THF)=1:1 and the green solution is then cooled, with stirring, to 3° C. under an inert gas atmosphere. 189 mg (5.00 mmol) of sodium borohydride are then added and the solution is warmed to 23° C. and stirred for 1.5 hour at this temperature. The reaction mixture is poured on 100 ml of water and the precipitated product is filtered and washed with 3×50 ml of water. The green residue is purified by flash chromatography (Ø4 cm, hexane/ethyl acetate=4:1), giving 1.27 g (80.1% of theory) of green solid mono(hydroxymethyl)-tetra(α-2,4-dimethyl-3-pentyloxy)palladium phthalocyanine having a $\lambda_{max}$ (NMP) of 706 nm.

IR spectrum (KBr): 3700–3120 (w), 2960–2880 (s), 1740 (w), 1600(s), 1590 (s). MALDI MS: (M+H)$^+$=1106.7 Da.

The NMR (500 MHz, CDCl$_3$) shows one single hydroxymethyl group which is in para-position one of the alkoxy radicals.

EXAMPLE A5

A 250 ml three-necked flask, equipped with magnetic stirrer, thermometer and nitrogen inlet, is charged with 0.79 g (0.74 mmol) of the monoformylated product of Example A2 in 100 ml of ethanol/THF=1:1 and the green solution is cooled, with stirring, to 5° C. under an inert gas atmosphere. Subsequently, 98 mg (2.59 mmol) of sodium borohydride are added and the solution is warmed to 23° C. and stirred for 2.5 hours at this temperature. The reaction mixture is then poured on 100 ml of water and extracted with 200 ml of ethyl acetate. The organic phase is washed with 3×50 ml of saturated NaCl solution and then dried over MgSO$_4$, filtered and concentrated by evaporation. The green residue is purified by flash chromatography (Ø4 cm, hexane/ethyl acetate=5:1), giving 0.57 g (72.5% of theory) of green solid mono(hydroxymethyl)-tetra(α-2,4-dimethyl-3-pentyloxy) copper phthalocyanine having a $\lambda_{max}$ (NMP) of 716 nm.

In a differential calorimeter (Perkin Elmer DSC-7, aluminium crucible, heating rate 10° C./min), the compound so obtained shows at 140–177° C. a small endothermic heat flow which is attributed to a glass transition.

IR spectrum (KBr): 3700–3120 (w), 2960–2880 (s), 1590 (s), 1500 (s), 1490 (s).

EXAMPLE A6

A 250 ml three-necked flask, equipped with magnetic stirrer, thermometer and nitrogen inlet, is charged with 1.21 g (1.21 mmol) of the monoformylated product of Example A3 in 100 ml of ethanol/THF=1:1 and the green solution is cooled, with stirring, to 4° C. under an inert gas atmosphere. Subsequently, 160 mg (4.24 mmol) of sodium borohydride ride are added and the solution is warmed to 23° C. and stirred for 1 hour at this temperature. The reaction mixture is poured on 100 ml of water and extracted with 200 ml of ethyl acetate. The organic phase is washed with 3×50 ml of saturated NaCl solution and then dried over MgSO$_4$, filtered and concentrated by evaporation. The green residue is purified by flash chromatography (Ø4 cm, hexanelethyl acetate=6:1), giving 1.11 9 (91.6% of theory) of green solid mono(hydroxymethyl)-tetra(α-2,4-dimethyl-3-pentyloxy) phthalocyanine having a $\lambda_{max}$ (NMP) of 716 nm and a side band of 742 nm.

IR spectrum (KBr): 3700–3120 (w), 2960–2880 (s), 1590 (s), 1490 (s). The NMR (300 MHz, CDCl$_3$) shows one single hydroxymethyl group which is in para-position to one of the alkoxy radicals.

EXAMPLE A7

A 50 ml three-necked flask, equipped with magnetic stirrer, thermometer and nitrogen inlet, is charged with 0.5 g (0.47 mmol) of the product of Example A5, 10 mg of 4-dimethylaminopyridine, 10 ml of pyridine and 5 ml of acetic anhydride and the green solution is stirred for 2 hours at 23° C. This mixture is then poured on 30 ml of water and the precipitated product is isolated by filtration and washed thoroughly with water. The green residue is purified by flash chromatography (Ø4 cm, hexane/ethyl acetate=9:1), giving 0.42 g (80.9% of theory) of green solid mono (acetoxymethyl)-tetra($\alpha$-2,4-dimethyl-3-pentyloxy)copper phthalocyanine having a $\lambda_{max}$ (NMP) of 714 nm.

IR spectrum (KBr): 2960–2880 (s), 1740 (m), 1590 (s), 1500 (s),1490 (s).

EXAMPLE A8

A 50 ml three-necked flask, equipped with magnetic stirrer, thermometer, reflux condenser, nitrogen inlet and oil bath, is charged with 0.5 g (0.50 mmol) of the product of Example A6, 1.10 g (5 mmol) of zinc acetate dihydrate and 20 ml of dichloromethane and the green solution is refluxed, with stirring, for 5 hours under an inert gas atmosphere. The solution is then concentrated by evaporation and the residue is purified by flash chromatography (Ø4 cm, hexane/ethyl acetate=10:1), giving 0.28 g (52.2% of theory) of green solid mono(hydroxymethyl)-tetra($\alpha$-2,4-dimethyl-3-pentyloxy) zinc phthalocyanine having a $\lambda_{max}$ (NMP) of 715 nm.

IR spectrum (KBr): 3700–3100 (m), 2960–2880 (s), 1590 (s), 1490 (s). Elemental analysis: theory 6.1% Zn, found 5.99% Zn.

EXAMPLE A9

A 250 ml three-necked flask, equipped with magnetic stirrer, thermometer, dropping funnel, reflux condenser and nitrogen inlet, is charged with 4.40 g (60.2 mmol) of DMF (dried over molecular sieve 4A) and cooled, with stirring, to 3° C. under an inert gas atmosphere. Over 5 min, 5.5 ml (60.2 mmol) of POCl$_3$ (freshly distilled) are added dropwise and the clear colourless liquid is then stirred for 30 min at 23° C. After adding 7.8 g (7.53 mmol) of tetra($\alpha$-2,4-dimethyl-3-pentyloxy)zinc phthalocyanine (prepared according to EP 492,508) in 80 ml of chlorobenzene (dried over molecular sieve 4A), the mixture is heated for 6 hours to 95° C. After cooling to 23° C., 7.8 g of sodium acetate in 34 ml of water are added and the mixture is stirred for 30 min. The mixture is extracted with 250 ml of ethyl acetate and the organic phase is washed with 100 ml of 10% NaHCO$_3$ solution and 3×50 ml of saturated NaCl solution and then dried over MgSO$_4$, filtered and concentrated by evaporation, giving 6.89 g of a green solid having a $\lambda_{max}$ (NMP) of 728 nm, which is a metal-free mixture of mono- and diformyl-tetra($\alpha$-2,4-dimethyl-3-pentyloxy) phthalocyanine.

A 1 litre three-necked flask, equipped with magnetic stirrer, thermometer and nitrogen inlet, is charged with 6.89 g (6.89 mmol) of this crude product and 500 ml of ethanol/THF=1:1 and the green solution is cooled, with stirring, to 4° C. under an inert gas atmosphere. Subsequently, 1.64 g (38.7 mmol) of sodium borohydride are added and the solution is warmed to 23° C. and stirred for 30 min at this temperature. The reaction mixture is poured on 250 ml of water and charged with 400 ml of ethyl acetate. The organic phase is washed with 3×100 ml of saturated NaCl solution and then dried over MgSO$_4$, filtered and concentrated by evaporation. The green residue is purified by flash chromatography (Ø9 cm, hexane/ethyl acetate=6:1), giving 4.70 g (61.5% of theory) of green solid monohydroxymethyl-tetra ($\alpha$-2,4-dimethyl-3-pentyloxy)phthalocyanine, which is identical to the product of Example A6 according to DC, UV and NMR, as well as 0.19 g (2.4% of theory) of di(hydroxymethyl)-tetra($\alpha$-2,4-dimethyl-3-pentyloxy) phthalocyanine [MALDI-MS: (M+H)$^+$=1033.2 Da].

EXAMPLE A10

A 50 ml three-necked flask, equipped with magnetic stirrer, thermometer, dropping funner, nitrogen inlet and reflux condenser, is charged with 0.83 ml (10.9 mmol) of DMF (dried over molecular sieve 4A) and cooled, with stirring, to 3° C. under an inert gas atmosphere. Over 5 min, 1 ml (10.9 mmol) of POCl$_3$ (freshly distilled) is added dropwise and the clear colourless liquid is then stirred for 30 min at 23° C. Subsequently, 2 g (1.81 mmol) of the monoformylated product of Example A1 in 20 ml of chlorobenzene are added drop-wise and the reaction mixture is stirred for 3.5 hours at 95° C. After cooling to 23° C., 2 g of sodium acetate in 8 ml of water are added and the mixture is stirred for 30 min. The mixture is extracted with 250 ml of ethyl acetate and the organic phase is washed with 50 ml of 10% NaHCO$_3$ solution and 3×50 ml of saturated NaCl solution and then dried over MgSO$_4$, filtered and concentrated by evaporation. The green residue is purified by flash chromatography (Ø9 cm, hexanelethyl acetate=8:1), giving 0.5 g (24.4% of theory) of green solid diformyl-tetra($\alpha$-2,4-dimethyl-3-pentyloxy)palladium phthalocyanine having a $\lambda_{max}$ (NMP) of 704 nm and a R$_f$ of 0.16 (silica gel, hexane/ethyl acetate 4:1).

IR (KBr): 3000–2840 (s), 1690 (s), 1590 (s), 1500(s). MALDI-MS: (M+H)$^+$=1132.9 Da.

The NMR (300MHz, CDCl$_3$) shows two aldehyde functions (12.55–12.49 ppm, m, 2H).

EXAMPLE A11

A 50 ml three-necked flask, equipped with magnetic stirrer, gas inlet tube and thermometer, is charged with 1 g (0.91 mmol) of the monoformylated product of Example A1 and 37 mg (0.54 mmol) of pyrazole in 20 ml THF and cooled, with stirring, to 3° C. Over 10 min, 48 mg (1.09 mmol) of sodium hydride are added in increments and the green solution is then stirred for 24 hours under a stream of air at 23° C. The solution is poured on 60 ml of ice water which is acidified with 1N HCl. The precipitate is purified by flash chromatography (Ø2 cm, hexane/ethyl acetate=4:1), giving 0.3 g (29.6% of theory) of green solid monocarboxy-tetra($\alpha$-2,4-dimethyl-3-pentyloxy)palladium phthalocyanine having a $\lambda_{max}$ (NMP) of 707 nm.

IR (KBr): 3640–3100 (s), 2980–2820 (m), 1710 (m), 1630(m) 1590 (m), 1480(m). MALDI-MS: (M+H)$^+$=1121.1 Da.

EXAMPLE A12

A 250 ml three-necked flask, equipped with magnetic stirrer, thermometer and nitrogen inlet, is charged with tetra($\alpha$-2,4-dimethyl-3-pentyloxy)paliadium phthalocyanine (prepared according to EP 703 280) and 0.47 g (6 mmol) of acetyl chloride in 50 ml of chlorobenzene. The mixture is cooled, with stirring, to 3° C. under an argon atmosphere. Subsequently, 0.65 g (2.5 mmol) of tin tetrachloride in 15 ml of chlorobenzene is added dropwise over 30 min and the mixture is stirred for 5 hours at 23° C. 50 ml of 3N HCl are then added and stirred for 5 min. The precipitate is dissolved in 300 ml of ethyl acetate, the phases are separated and the organic phase is washed with 100 ml of 1N NaOH and 3×100 ml of saturated NaCl solution until neutral. The solution is dried over MgSO$_4$, filtered and concentrated by evaporation. The crude product, still containing educt, is purified by flash chromatography (Ø9 cm, hexane/ethyl acetate=6:1), giving 0.59 g (10.5% of theory) of green solid monoacetyl-tetra(α-2,4-dimethyl-3-pentyloxy)palladium phthalocyanine having a $\lambda_{max}$ (NMP) of 704 nm.

IR (KBr): 3000–2840 (m), 1690 (m), 1590 (s), 1490(s). MALDI-MS: (M+H)$^+$=1120.0 Da.

The NMR (500 Mz, CDCl$_3$) shows that the acetyl group has been introduced selectively in para-position to one of the alkoxy groups.

EXAMPLE B1

A 2% solution of the product of Example A7 in methylcyclohexane is spin coated on a 1.2 mm polycarbonate substrate having a diameter of 12 cm with grooves 180 nm deep and 0.5 μm wide at a distance of 1.6 μm from each other. A gold layer is vapour-deposited on this coat and a UV-curable protective layer is then applied thereon. Signals are inscribed into the recording layer on a Philips CD-R engine apparatus at double (2×) or quadruple (4×) recording speed using a semiconductor diode which emits at 780 nm. The maximum jitter determined on a Philips CD920JT read tester apparatus at single (1×) readout speed is significantly better than that of tetra(α-2,4-dimethyl-3-pentyloxy)copper phthalocyanine prepared according to EP 703 281:

| Optical density | 2×: Jitter$_{max}$ [ns] | 4×: Jitter$_{max}$ [ns] |
|---|---|---|
| 0.50 | 42 | 35 |
| 0.57 | 35 | 30 |

EXAMPLE B2

A 2% solution of the product of Example A5 in methylcyclohexane is spin coated on a 1.2 mm polycarbonate substrate having a diameter of 12 cm and grooves 180 nm deep and 0.5 μm wide at a distance of 1.6 μm from each other. A gold layer is vapour-deposited on this coat and a UV-curable protective layer is then applied thereon. Signals are inscribed into the recording layer on a Philips CD-R engine apparatus at single (1×) recording speed using a semiconductor diode which emits at 780 nm. The maximum jitter determined on a Philips CD920JT read tester apparatus at single (1×) readout speed is significantly better than that of tetra(α-2,4-dimethyl-3-pentyloxy)copper phthalocyanine prepared according to EP 703 281:

| Laser intensity [mW] | 1×: Jitter$_{max}$ [ns] |
|---|---|
| 5.0 | 35 |
| 5.6 | 30 |
| 6.2 | 30 |
| 6.8 | 27 |
| 7.5 | 27 |
| 8.1 | 27 |
| 8.8 | 26 |
| 9.5 | 25 |

What is claimed is:
1. A compound of formula I

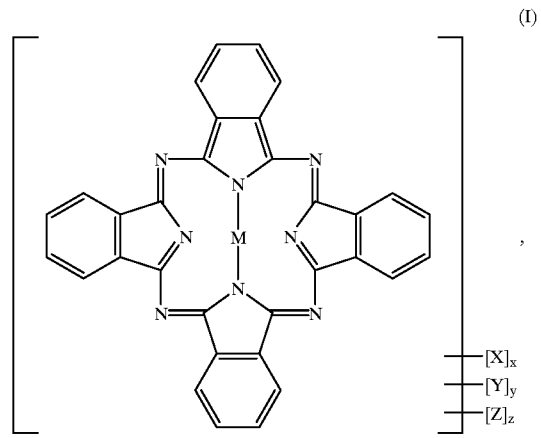

wherein

M is a divalent metal, oxometal, halogenometal or hydroxymetal, or 2 hydrogen atoms, X is halogen, or 2 X in vicinal position on a phenyl ring form together a —C=C—C=C— bridge so that an additional phenyl ring is obtained, Y is —OR$_1$, —OOC—R$_2$, —NHR$_1$, —N(R$_1$)R$_2$ or —SR$_1$, Z is —CHO, —CH(OR$_3$)OR$_4$, —CH=N—OH, —CH=N—OR$_3$, —CH=N—NHR$_5$, —CH=N—N(R$_3$)R$_5$, —CH$_2$OH, —CH$_2$OR$_3$, —CH$_2$OOC—R$_3$, —CO—R$_3$, —COOH or —COOR$_3$, x is 0 or a number from 1 to 8, y depending on z is a number from z to 4, and z is a number from 1 to 4, wherein R$_1$ to R$_5$ are each independently of one another C$_1$–C$_{20}$alkyl which is unsubstituted or substituted by halogen, hydroxy, C$_1$–C$_{20}$alkoxy, C$_1$–C$_{20}$alkylamino or C$_2$–C$_{20}$dialkylamino and which may be interrupted by —O—, —S—, —NH— or —NR$_6$—; C$_1$–C$_{20}$cycloalkyl, C$_1$–C$_{20}$alkenyl, C$_1$–C$_{20}$cycloalkenyl, C$_1$–C$_{20}$alkynyl, C$_1$–C$_{20}$cycloalkynyl, C$_6$–C$_{18}$aryl or C$_7$–C$_{18}$aralkyl, or R$_1$ and R$_2$ together are C$_2$–C$_{20}$alkylene which is unsubstituted or substituted by oxo, hydroxy or C$_1$–C$_{20}$carboxy and which may be interrupted by —O—, —S—, —NH— or —NR$_6$—, or R$_3$ and R$_4$ together are C$_2$–C$_{20}$alkylene which is unsubstituted or substituted by halogen, hydroxy, C$_1$–C$_{20}$alkoxy, C$_1$–C$_{20}$alkylamino or C$_2$–C$_{20}$dialkylamino, and R$_6$ is C$_1$–C$_{20}$alkyl, C$_1$–C$_{20}$cycloalkyl, C$_1$–C$_{20}$alkenyl, C$_1$–C$_{20}$cycloalkenyl, C$_1$–C$_{20}$alkynl, C$_1$–C$_{20}$cycloalkynyl, C$_6$–C$_{18}$aryl or C$_7$–C$_{18}$aralkyl, and wherein the divalent oxometal, halogenometal or hydroxymetal may be additionally coordinated to one, and the divalent metal atom may additionally be coordinated to one or two, neutral molecules which are independent or dependent on one another, which neutral molecules contain at least one hetero atom selected from the group consisting of N, O and S.

2. A compound according to claim 1, wherein M is $H_2$, Cu(II), Zn(II), Ni(II), Pd(II), Pt(II), Mn(II) or Co(II), preferably $H_2$, Cu(II), Zn(II) or Pd(II) and, particularly preferably, Cu(II).

3. A compound according to claim 1, wherein X is chloro.

4. A compound according to claim 1, wherein Y is —$OR_1$ or —OOC—$R_2$, preferably —OR.

5. A compound according to claim 1, wherein Z is —CHO, —CH($OR_3$)$OR_4$, —$CH_2OH$, —$CH_2OOC$—$R_3$, —CO—$R_3$, —COOH or —$COOR_3$.

6. A compound according to claim 1, wherein x is 0, y is 2, 3 or 4, z is 1 or 2, and Y is —$OR_1$, wherein $R_1$ is secondary unsubstituted $C_4$–$C_8$alkyl which is branched several times.

7. A compound according to claim 6, wherein y is 4.

8. A compound according to claim 1 of formula IIa, IIb, IIc or IId, (IIa)

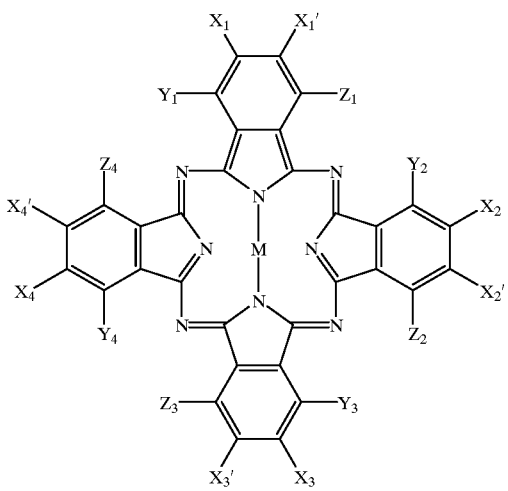

(IIb)

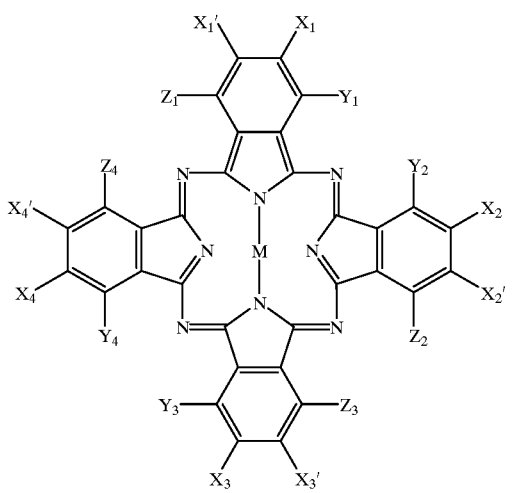

(IIc)

(IId)

or a mixture of two or more compounds selected from the compounds of formulae IIa, IIb, IIc and IId, wherein M is a divalent metal, oxometal, halogenometal or hydroxymetal, or 2 hydrogen atoms, $X_1$ to $X_4$ and $X_1'$ to $X_4'$ are each indenpendently of one another hydrogen or halogen, $Y_1$ to $Y_4$ are each independently of one another hydrogen or —$OR_1$, $Z_1$ is —CHO, —CH($OR_3$)$OR_4$, —CH=N—OH, —CH=N—$OR_3$, —CH=N—$NHR_5$, —CH=N—N($R_3$)$R_5$, —$CH_2OH$, —$CH_2OR_3$, —$CH_2OOC$—$R_3$, —CO—$R_3$, —COOH or $COOR_3$, and $Z_2$ to $Z_4$ are each independently of one another hydrogen or a group $Z_1$, with the proviso that the number of those substituents $Y_1$ to $Y_4$ which are not hydrogen is at least equal to the number of those substituents $Z_1$ to $Z_4$ which are not hydrogen, and where $R_1$ to $R_5$ are as defined in claim 2, and the divalent oxometal, halogenometal or hydroxymetal may additionally be coordinated to one, and the divalent metal atom may additionally be coordinated to one or two, neutral molecules which are independent or dependent on one another, which neutral molecules contain at least one hetero atom selected from the group consisting of N, O and S.

9. A process for the preparation of a compound of formula III

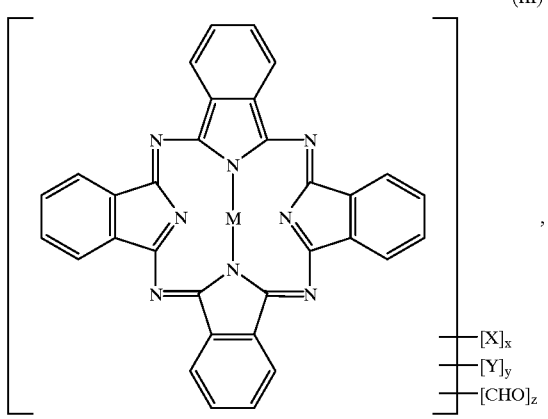

(III)

wherein M, X, Y, x, y and z are as defined for formula I, by reacting 1 mol of a compound of formula IV

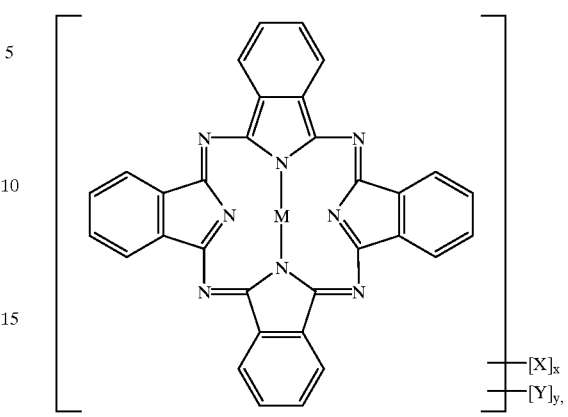

(IV)

wherein M, X, Y, x and y are as defined in claim 1 for formula III, with z mol each of dimethylformamide and phosphoryl chloride.

10. A process according to claim 9, which comprises first reacting equimolar amounts of dimethylformamide and phosphoryl chloride under inert gas, then adding the phthalocyanine to be formylated dissolved in an inert solvent and subsequently raising the temperature.

11. A process according to claim 10, which comprises raising the temperature to 50 to 100° C.

12. An optical recording medium, which comprises a substrate, a recording layer and a reflecting or partially reflecting layer, wherein the recording layer comprises a compound as claimed in claim 1.

* * * * *

UNITED STATES PATENT AND TRADEMARK OFFICE
CERTIFICATE OF CORRECTION

PATENT NO. : 6,087,492
DATED : July 11, 2000
INVENTOR(S) : Heinz Wolleb

It is certified that error appears in the above-identified patent and that said Letters Patent is hereby corrected as shown below:

Column 19,
Line 5, Claim 3 should read:
-- 3. A compound according to claim 1, wherein X is chloro or bromo. --.

Signed and Sealed this

Fourth Day of January, 2005

JON W. DUDAS
*Director of the United States Patent and Trademark Office*